(12) United States Patent
Brennan et al.

(10) Patent No.: US 6,200,937 B1
(45) Date of Patent: *Mar. 13, 2001

(54) ANTI-RESIDUE SHAMPOO AND LIQUID TOILETRY PRODUCTION METHOD

(75) Inventors: Robert Brennan, Mercerville, NJ (US); Abizer Gaslightwala, Cambridge, MA (US); Nelson L. Perassinoto, Sao Paulo (BR); Rafael Delgado, Nutley, NJ (US); Arthur Pellegrino; Steve Aridgides, both of Yardley, PA (US); Charles L. Adams, Flemington, NJ (US); Carol J. Collins, Granada Hills, CA (US)

(73) Assignee: Neutrogena Corporation, Los Angeles, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/094,384

(22) Filed: Jun. 9, 1998

(51) Int. Cl.[7] ................................. C11D 1/62; C11D 1/65
(52) U.S. Cl. ..................... 510/119; 510/121; 510/122; 510/123; 510/124; 510/125; 510/147; 510/151; 510/405; 510/426; 510/428; 510/473
(58) Field of Search ................................. 510/119, 121, 510/122, 123, 124, 125, 147, 151, 405, 426, 428, 473

(56) References Cited

U.S. PATENT DOCUMENTS

| | | | |
|---|---|---|---|
| 3,256,181 | 6/1966 | Zingg et al. | 252/8.55 |
| 3,423,075 | 1/1969 | Knudsen et al. | 259/8 |
| 3,606,270 | 9/1971 | Zimmerly | 259/8 |
| 3,871,625 | 3/1975 | Iwako | 259/8 |
| 3,998,433 | 12/1976 | Iwako | 259/8 |
| 4,002,324 | 1/1977 | Huet | 259/9 |
| 4,089,050 | 5/1978 | Huet | 366/181 |
| 4,092,738 | 5/1978 | Doom | 366/304 |
| 4,175,873 | 11/1979 | Iwako et al. | 366/165 |
| 4,239,396 | 12/1980 | Arribau et al. | 366/2 |
| 4,327,759 | 5/1982 | Millis | 137/3 |
| 4,453,829 | 6/1984 | Althouse, II | 366/13 |
| 4,511,256 | 4/1985 | Karg et al. | 366/165 |
| 4,729,663 | 3/1988 | Karg | 366/165 |
| 4,767,217 | 8/1988 | Van den Brink et al. | 366/168 |
| 4,808,004 | 2/1989 | McIntire et al. | 366/155 |
| 4,850,702 | 7/1989 | Arribau et al. | 366/136 |
| 4,850,704 | 7/1989 | Zimmerly et al. | 366/263 |
| 4,955,723 | 9/1990 | Schmeider | 366/155 |
| 5,009,880 | 4/1991 | Grollier et al. | 424/47 |
| 5,085,513 | 2/1992 | Ivarson | 366/150 |
| 5,322,357 | 6/1994 | Mazer | 366/306 |
| 5,391,368 | 2/1995 | Gerstein | 424/70.13 |
| 5,501,524 | 3/1996 | Zuidema | 366/181.4 |
| 5,540,499 | 7/1996 | Seeger | 366/178.1 |
| 5,580,494 | * 12/1996 | Sandhu et al. | 510/125 |
| 5,589,177 | * 12/1996 | Herb et al. | 424/401 |
| 5,599,102 | 2/1997 | Hamada et al. | 366/178.1 |
| 5,672,576 | * 9/1997 | Behrens et al. | 510/127 |
| 5,720,964 | * 2/1998 | Murray | 424/401 |
| 5,726,137 | 3/1998 | Patel et al. | 510/122 |
| 5,776,444 | * 7/1998 | Birtwistle et al. | 424/70.12 |
| 5,783,200 | * 7/1998 | Motley et al. | 424/401 |

FOREIGN PATENT DOCUMENTS

| | | | |
|---|---|---|---|
| 0 443 324 B1 | 8/1991 | (EP) . | |
| 0 605 395 A1 | 7/1994 | (EP) . | |
| 0 570 335 B1 | of 1995 | (EP) . | |
| WO 81/02531 | 9/1981 | (WO) . | |
| WO 87/07819 | 12/1987 | (WO) . | |
| WO 91/07262 | 5/1991 | (WO) . | |
| WO 92/11927 | 7/1992 | (WO) . | |
| WO 93/08787 | 5/1993 | (WO) | A61K/7/06 |
| WO 94/15886 | 7/1994 | (WO) . | |
| WO 95/03120 | 2/1995 | (WO) . | |
| WO 96/10455 | 4/1996 | (WO) . | |
| WO 96/14140 | 5/1996 | (WO) . | |
| WO 96/21505 | 7/1996 | (WO) . | |
| WO 97/35543 | 10/1997 | (WO) | A61K/7/06 |
| WO 97/36674 | 10/1997 | (WO) . | |
| WO 97/33555 | 9/1998 | (WO) | A61K/7/06 |

OTHER PUBLICATIONS

"Quadro™ Ytron®, The Latest Technology for Wet Mixing" Brochure By Quadro Engineering Inc. (1994).
"Quadro™ Ytron®, Owner's Guide", Brochure by Quadro Engineering Inc. (Jan.–Feb. 1996).

* cited by examiner

*Primary Examiner*—Yogendra Gupta
*Assistant Examiner*—Charles Boyer

(57) ABSTRACT

Detergent compositions, including, but not limited to, anti-residue shampoos, are provided which include one or more anionic surfactants, an anionic polymer, a mono cationic conditioning agent, and a cationic polymer. These shampoos are preferably clear. Additionally, there is provided a recirculatory batch processor which includes a disperser and at least one pump selected from a supply pump and a return pump. The pump is in communication with the disperser. Furthermore, a recirculatory batch process is provided which includes the steps of delivering, at a first rate, a liquid from a tank to a recirculatory batch processor as described above; during the delivery, dispersing solids into the liquid to produce a liquid containing dispersed solids; and during the delivery, returning, at a second rate, the liquid containing dispersed solids to the tank; wherein the second rate is greater than the first rate.

15 Claims, 3 Drawing Sheets

ANTI-RESIDUE SHAMPOO AND LIQUID TOILETRY PRODUCTION METHOD

FIELD OF THE INVENTION

This invention relates to detergent compositions such as, for example, anti-residue shampoos for dry or damaged hair. This invention also relates to a method for the production of such detergents compositions, which also include, but are not limited to, other liquid toiletry compositions such as baths, gels, washes, lotions, cremes, ointments, facial cleansers, body cleansers, sunblocks, mouth rinses and the like.

BACKGROUND OF THE INVENTION

Shampoos typically include surfactants, conditioners, and styling aids. However, surfactant residue, styling aid residue, and cationic build-up from conditioners cause hair to become dull, flat, and unmanageable. Although some shampoos can remove cationic build-up, they cause the hair to become frizzy, dry, and unmanageable. Therefore, there is a need for a shampoo which can remove dirt, oil, surfactant residue, conditioner residue, and styling aid residue that build up in hair, while leaving the hair in a non-stripped, non-drying, and conditioned state. The residue in hair is typically predominantly conditioner.

Additionally, the ingredients used in formulating a liquid shampoo and other liquid toiletries are often supplied in solid or powder form. Consequently, it is necessary to disperse these solids or powders in liquid solutions in order to formulate the shampoo or other liquid toiletry product.

Various dispersers and methods for dispersing solids into liquid solutions have been developed over the years. See, U.S. Pat. Nos. 3,256,181; 3,423,075; 3,606,270; 3,871,625; 3,998,433; 4,002,324; 4,092,738; 4,175,873; 4,239,396; 4,327,759; 4,453,829; 4,511,256; 4,767,217; 4,808,004; 4,850,702; 4,850,704; 4,955,723; 5,085,513; 5,322,357; 5,501,524; 5,540,499; and 5,599,102. For example, U.S. Pat. No. 5,085,513 describes an apparatus for continuously mixing a powder and a liquid together.

However, continuous or in-line processing methods are not well suited to the rapidly changing processing needs of the liquid toiletry industry because the equipment used to make a particular formula tends to be highly formula-specific. Thus, changes to a formula or attempts to make products having different formulas in continuous process equipment often give rise to significant modifications to the equipment used to make these formulas. Therefore, shampoos and other liquid toiletries are often produced by the more flexible batch processing method, where all of the processing steps are performed in one vessel known as a "batch reactor". These processing steps can include, for example, liquid/solids mixing, heating/cooling, homogenization, and raw material addition. An advantage of batch processing is that it requires only one piece of equipment to produce a complete batch of product.

Present batch processing methods are not without their disadvantages, however. Firstly, as the batch size increases, the batch processing equipment escalates in complexity and cost. Additionally, there typically is less control over processing parameters, such as temperature and particle distribution in a batch process relative to that in a continuous process. Furthermore, overall processing efficiency decreases.

The batch reactor also presents scale-up problems in the transition from a pilot batch reactor to a production scale version. It is difficult to correlate mixing speeds and times, heating and cooling rates, and other parameters for batch reactors that vary in size, shape, and geometry. Often, development work performed for a pilot batch reactor must be duplicated during production version scale-up.

Another disadvantage of batch reactors is the limited range of batch sizes possible. This limits the flexibility of batch processes and often requires duplicate equipment to meet production needs.

Lastly, a batch reactor is difficult to retrofit with technological improvements. For example, replacing an in-tank homogenizer in a batch reactor with a new and improved in-line homogenizer may be difficult or impossible. This is a significant drawback because a batch reactor may quickly become obsolete due to its inability to be retrofitted with improved components.

Therefore, both continuous in-line processes and present batch processes are inadequate to meet current processing requirements. The present inventors have discovered a recirculatory batch process (RBP) and related equipment which achieve the advantages of a continuous in-line processing system, i.e., minimal scale-up difficulties, reasonable cost, lack of batch size dependency, and adaptability for retrofitting, but in a batch process system.

SUMMARY OF THE INVENTION

According to one embodiment of the present invention, there are provided detergent compositions such as, for example, shampoos which include one or more anionic surfactants, an anionic polymer, a mono cationic conditioning agent, and a cationic polymer. The detergent compositions may be anti-residue shampoos. These shampoos are preferably clear. The detergent compositions may also exhibit enhanced rinsability, i.e. in the amount of residue remaining after rinsing is decreased.

According to another embodiment of the present invention, there is provided a recirculatory batch processor which includes a disperser and at least one pump selected from a supply pump and a return pump. The pump is in communication with the disperser. The supply pump is for delivering liquids from a tank to the disperser. The return pump is for removing liquids from the disperser and for returning liquids to the tank. The disperser is preferably a high-shear powder/solids disperser.

A third embodiment of the present invention provides a recirculatory batch process which includes the steps of delivering, at a first rate, a liquid from a tank to a recirculatory batch processor; during the delivery, dispersing solids into the liquid to produce a liquid containing dispersed solids; and during the delivery, returning at a second rate the liquid containing dispersed solids to the tank; wherein the second rate is greater than the first rate. These steps can be repeated to increase the amount of dispersed solids in the liquid. The processor is as described above.

DETAILED DESCRIPTION OF THE INVENTION

Figure 1:
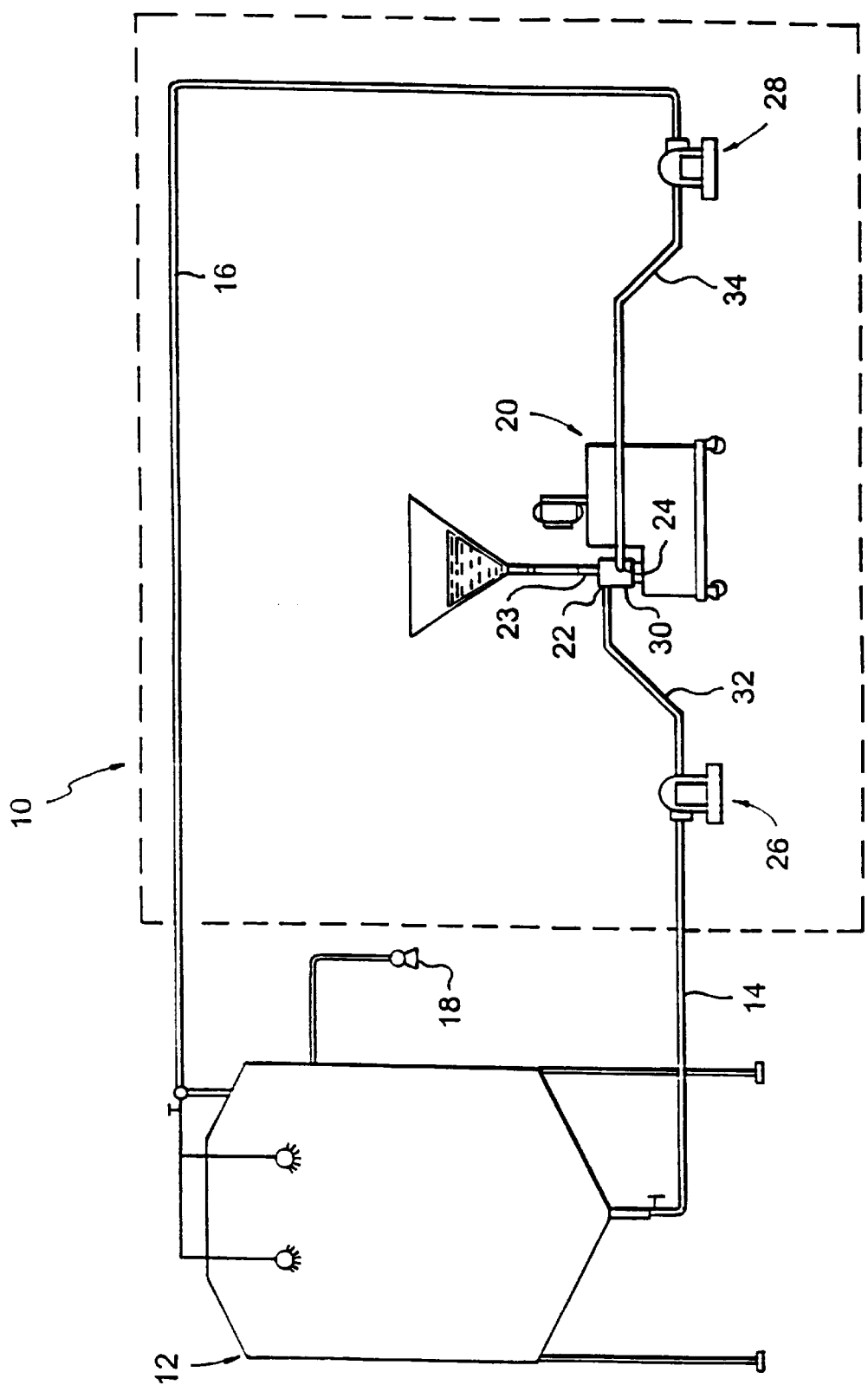
FIG. 1 is a schematic diagram of an embodiment of a recirculatory batch process system according to the present invention.

The detergent compositions of the present invention include at least one anionic surfactant (and preferably two), an anionic polymer, a mono cationic conditioning agent, and a cationic polymer. The detergent compositions may be, for example, antiresidue shampoos. These shampoos remove surfactant residue, styling aid residue, and cationic build-up from hair to keep hair manageable and to condition the hair. They are preferably clear, as opposed to opaque or hazy, but may be colored or tinted, as well. Furthermore, these shampoos exhibit enhanced rinsability to leave little, if any, organic residue from the shampoo in the hair treated with the shampoo.

Anionic surfactants in a shampoo remove dirt, oil, surfactant residue and styling aid residue from the hair. These surfactants have a fatty hydrophobic moiety, which has an affinity for dirt and oils, and a long chain hydrophilic tail which has an affinity for water. The hydrophobic portion of the anionic surfactant attaches to the dirt and oil along the hair shaft during lathering of the shampoo. When the shampoo is rinsed away, the hydrophilic tail attaches itself to the water and the surfactant moiety is pulled off the hair strand taking with it the dirt and oil. Anionic surfactants suitable for use in the present invention include, but are not limited to, ammonium lauryl sulfate, sodium laureth sulfate, and mixtures thereof.

The total amount of anionic surfactant may vary, but typically is a surfactant and styling aid residue removing effective amount. Preferably, the amount ranges, on a weight basis, from about 5% to about 25%, based upon total weight of the detergent composition. Most preferably, the amount is from about 10% to about 15% by weight, based upon total weight of the composition.

The anionic polymer component of the compositions of the present invention is believed to form a strong complex with the cationic build-up in the hair to remove any cationic build-up from hair follicles. Hair keratin is negatively charged. The more damaged the hair, the greater the negative charge. Cationic build-up is believed to form as a result of a strong affinity for hair keratin by the positively charged cationic materials in conditioning agents.

The anionic polymer, which has a relatively high molecular weight in comparison to hair keratins, has a greater negative charge than that of the hair. As a result, the cationic material is believed to form a strong complex with the anionic polymer, thus removing the cationic build-up from the hair follicle.

The relatively high molecular weight of the anionic polymer, in comparison to the other primary components of the detergent composition, also contributes to the mildness of the detergent composition. Anionic polymers suitable for use in the present compositions include, but are not limited to, sodium polystyrene sulfonate.

The amount of anionic polymer may vary, but typically will be a cationic build-up removing effective amount. Preferably, the amount ranges, on a weight basis, from greater than 0% to about 5%, based upon total weight of the detergent composition. Most preferably, the amount is from about 0.1% to about 1% by weight, based upon total weight of the composition.

The mono cationic conditioning agent component of the detergent composition conditions the hair. The mono cationic conditioning agent also acts with the cationic polymer to increase the effectiveness of the cationic polymer. Mono cationic conditioning agents suitable for use herein include, but are not limited to, bishydroxyethyldihydroxypropyl stearaminium chloride, cetrimonium chloride, and mixtures thereof.

The amount of mono cationic conditioning agent may also vary, but typically is a dry-hair conditioning effective amount. Preferably, the amount ranges, on a weight basis, from greater than 0% to about 5%, based upon total weight of the detergent composition. Most preferably, the amount is from about 0.1% to about 1% by weight, based upon total weight of the composition.

The cationic polymer of the composition conditions hair, including dry and damaged hair. Suitable cationic polymers include cationic cellulosic derivatives including, but are not limited to, polyquarternium 10, polyquarternium 11, and mixtures thereof. Preferably, the cationic polymer is highly substituted having a cationic substitution ranging from about 0.3 to about 0.6. Most preferably, the cationic polymer is polyquarternium 10 having a cationic substitution ranging from about 0.32 to about 0.52.

The amount of cationic polymer may vary, but typically is a hair conditioning effective amount. Preferably, the amount ranges, on a weight basis, from greater than 0% to about 2.5%, based upon total weight of the detergent composition. Most preferably, the amount ranges from about 0.1% to about 0.5% based upon total weight of the composition.

Preferably, the pH of the detergent composition ranges from about 5.5 to about 6.5.

The combination of a cationic polymer and an anionic polymer often produces an insoluble precipitate due to the cationic-anionic interaction. Therefore, a cationic polymer which does not react with the anionic polymer to produce an insoluble precipitate is preferred. For example, a shampoo according to the present invention which contains polyquarternium 10 having a molecular weight of about 300,000 and a cationic substitution ranging from about 0.32 to about 0.52, and sodium polystyrene sulfonate is clear. Other cationic polymers, including polyquarternium 11 and polyquarternium 10 versions having a lower cationic substitution than about 0.3 may produce a shampoo which is hazy. Preferably, the weight ratio of the anionic polymer to the cationic polymer ranges from about 5:1 to about 1:1.

Additional components typically used in the preparation of shampoos may be added. Such additives include, but are not limited to, anti-oxidants; humectants, such as glycerin and hydrotriticum wheat amino acid (hydrotriticum WAA); foam stabilizers including, but not limited to, non-ionic foam stabilizers such as cocodiethanolamide; metal chelating agents including, but not limited to, disodium ethylene diamine tetra acetic acid (disodium EDTA) or tetrasodium EDTA; purified or deionized water; anti-microbial agents including, but not limited to, dimethyldimethylol hydantonin (DMDMH); ultra-violet (UV) stabilizers; cationic silicones including, but not limited to, trimethylsilylamodimethicone; preservatives including, but not limited to, methylparaben and ethylparaben; fragrances; colorants including, but not limited to, D&C violet #2 and FD&C green #3; amphoteric surfactants including, but not limited to, cocamidopropyl betaine; citric acid; witch hazel; panthenol; linoleamidopropyl PG dimonium chloride phosphate; or any combination of any of the foregoing.

A detergent composition according to the present invention may be prepared as follows. An anionic polymer is diluted in water and betaine. The ratio of anionic polymer to water, by weight, is preferably from about 1:50 to about 1:70. The ratio of anionic polymer to betaine, by weight, is preferably from about 1:10 to about 1:15. The diluted anionic polymer is stirred for about 5 minutes. A cationic polymer is then added at ambient temperature and pressure. The solution is heated to from about 60° C. to about 70° C. for about 15 to about 30 minutes. A chelator and a pH buffer are added while maintaining heating at from about 60° C. to about 70° C. The heating is then discontinued. An anionic surfactant and a thickener are added while stirring the solution. Finally, a mono cationic conditioning agent is added.

The process and order of raw material addition may affect the clarity of the product, due to the fact that there is a large charge opposition and distribution by the raw materials themselves. Therefore, it is desirable to minimize opposite charge interaction. One method of preparing a detergent composition according to the present invention, while minimizing opposite charge interaction, is first to dilute the anionic polymer, such as, for example, sodium polystyrene sulfate in water and cocamidopropyl betaine. Then the cationic polymer, such as, for example, polyquarternium 10 is added to the solution. Upon complete hydration, the pH is buffered. Other raw materials, such as, for example, ammonium lauryl sulfate, sodium laureth sulfate, and cocamide DEA are then added to the solution.

Hair may be cleaned by applying to the hair, a hair cleaning effective amount of the detergent compositions described herein. Residue may be reduced in hair by applying to the hair a residue reducing effective amount of the detergent compositions described herein.

The detergent compositions of the present invention typically are prepared from one or more ingredients which are supplied in solid or powder form. For example, polyquartenium 10 is supplied in powder form. Such solid and powder ingredients may be added to shampoos and other liquid toiletries, such as baths, gels, washes, lotions, cremes, ointments, facial cleansers, body cleansers, sunblocks, mouth rinses, and the like, by a recirculatory batch process according to the present invention. The powders may be waxy solids having limited water solubility and water-insoluble inorganic solids. Compositions made according to the process of the invention may be either homogenous containing a single phase, or heterogeneous, such as dispersions of solids in one or more liquid phases. The liquid phase may be water-insoluble, Also, the liquid phase may be a single aqueous phase, a single organic phase, or a single mixed aqueous-organic phase. Alternatively, the liquid phase may be an emulsion having separate aqueous and organic phases with one phase suspended in the other phase.

The recirculatory batch process uses a processing platform or skid which is preferably a modular unit that may be moveable and can be connected to a batch processing tank. Use of such a processing platform permits the transfer of much or all of the processing from the tank to the recirculatory batch processing platform or skid, resulting in improved process turndown and product consistency and reductions in product cycle time.

One embodiment of a recirculatory batch processor is illustrated in FIG. 1. This recirculatory batch processor is a platform or skid 10 and includes a supply pump 26, a return pump 28, a disperser 20, and associated piping and valving. The processor is connected to a tank 12 through a supply line 14 and a return line 16. Individual liquid feeds are supplied to the tank through lines not shown in FIG. 1. Supply pump 26 is connected to the disperser 20 via line 32. The disperser 20 is connected to the return pump 28 via line 34. The type of tank interfaced with skid 10 is not critical since much of the processing occurs in the skid 10 rather than in the tank 12. However, a stirred tank is preferred.

The tank 12 contains a liquid to be processed. If the formulation to be prepared requires vacuum, for example to degas the formulation, a vacuum pump 18 may be attached to the tank 12 for this purpose. The supply line 14 is preferably connected near the bottom of tank 12 while the return line 16 is preferably connected near the top of tank 12 to promote efficient mixing of the liquid during processing. The location of the supply line 14 and return line 16 may vary as long as the supply line 14 is in communication with the liquid in the tank 12.

Line 32 is in communication, optionally through a valve, with a first inlet 22 of the disperser 20. Liquid from the tank passes through line 14, through pump 26, through line 32 into the first inlet 22 of the disperser 20. The disperser 20 disperses solids or powders into the liquid flowing through it to produce a liquid containing dispersed solids. These solids may remain suspended in the liquid in the case of insoluble materials, or they may be dissolved in the liquid in the case of soluble materials. Preferably, the disperser 20 is a high-shear powder/solids disperser, such as a Quadro Ytron (R) Model No. ZC-1 disperser manufactured by Quadro Process Inc., Waterloo, Ontario, Canada. See, U.S. Pat. Nos. 4,511,256 and 4,729,663.

The solids or powders enter the disperser 20 through a second inlet 23 to the disperser 20. Preferably, the solids or powders are introduced into the disperser 20 through a feeder such as, for example, an auger feeder or a gravity-flow hopper, such as the gravity-flow hopper in the Quadro Ytron (R) Model No. ZC-1 disperser. Large or irregularly shaped particles should be added to the disperser at a controlled rate to prevent powder handling problems such as "bridging" or "ratholing."

Line 34 is connected, optionally through a valve, to an outlet 24 of the disperser 20.

A chamber 30 in the disperser 20 is in communication with the inlets 22 and 23 and outlet 24. Preferably, the chamber 30 of the disperser 20 contains a rotor and a stator to mix the solids or powders with the liquid, such as in the Quadro Ytron (R) Model No. ZC-1 disperser. The rotor in combination with the stator creates a vacuum in the disperser 20. In general, consistent solids addition relies on a reduced pressure in the disperser to draw solids into the disperser.

Although the disperser 20 may be capable of creating a vacuum of about −25" Hg, as the fluid viscosity increases (i.e., >150 cP), the disperser may be less capable of creating a sufficient vacuum for incorporating dry materials into a fluid. The vacuum in the throat of the disperser is also limited by the vapor pressure of the liquid circulating through the processor. As vapor pressure of a liquid increases with increasing temperature, it is advantageous to limit the temperature of the circulating liquid to maximize the vacuum in the disperser to facilitate drawing of solids into the circulating liquid.

Attached to the supply line 14 and line 32, between the tank 12 and the disperser 20, is the supply pump 26. The supply pump 26 delivers the liquid contained in the tank 12 to the disperser 20. The supply pump 26 may be, but is not limited to, a positive displacement pump or a centrifugal pump. Preferably, the supply pump 26 is a positive displacement pump since such pumps are generally effective on fluids over a broad range of viscosities.

Line 34 connects the disperser 20 with the return pump 28. The return pump 28 returns the processed liquids from the outlet 24 of the disperser 20 via lines 16 and 34 to the tank 12 and preferably the top of the tank 12. The return pump 28 pumps at a greater rate than the supply pump 26. The return pump 28 may also be, but is not limited to, a positive displacement pump or a centrifugal pump. Preferably, the return pump 28 is a positive displacement pump.

By varying the mass flow rates of liquid through pumps 26 and 28, the pressure at the second inlet 23 of the disperser 20 may be controlled to ensure good solids addition under a variety of processing conditions.

Depending on such variables as the elevation of the disperser 20 relative to tank 12, the viscosity of the circulating liquid, and the desired mass flow rates, one or the other of pumps 26 and 28 may not be required. For example, if the liquid has a sufficiently low viscosity and the disperser 20 is positioned at an elevation below the bottom of tank 12, pump 26 may not be required. Likewise, if the disperser 20 is positioned at an elevation near the top of tank 12, the return pump 28 may not be required. However, as the viscosity of the liquid increases, the mass flow through the disperser 20 may be insufficient to create a vacuum adequate to mix the solids or powders with the liquid solution and both pumps 26 and 28 may be required to drive the liquid through the disperser 20 and to circulate the liquid between the tank 12 and the platform 10. The use of both the supply pump 26 and the return pump 28 is preferred as it provides the maximum flexibility in handling liquids over a range of viscosities and permits better control of the process.

In general, the liquid should be supplied to the disperser 20 at a pressure of at least about 10 to about 15 psig. The pressure of the liquid at the discharge of pumps 26 and 28 will depend on the configuration of the piping and equipment and the presence of any other process equipment between supply pump 26 and the disperser 20 and between the return pump 28 and the tank 12.

The liquid may be recirculated through the tank 12 and the disperser 20 until solids or powders addition is complete, i.e., the desired concentration of solids or powders in the liquid solution is achieved. However, the disperser 20 may be effective enough that only a single pass would be needed to incorporate powders, such as carbopol, titanium dioxide, zinc oxide, xanthan gums, and mixtures thereof, directly into liquids.

Other processing units including, but not limited to, heating, cooling, and homogenization units, may be added to the process loop, either upstream or downstream of the disperser. For example, a homogenizer such as a Quadro (TM) Z3 may be attached to the return line 16. Also, a heat exchanger, such as an in-line plate-type heat exchanger or a jacketed tank, may be attached to either line 32 or to return line 16 to heat or cool the liquid rapidly during processing. Preferably, the heat exchanger is an in-line plate-type heat exchanger since this type is generally more efficient than other types of heat exchangers. For example, cooling a toiletry preparation from 80° C. to 35° C. with 25° C. cooling water may require only 30 to 40% as much time with an in-line plate-type heat exchanger as compared to the time required to cool the batch with cooling coils contained in a jacketed tank.

Instrumentation, such as flowmeters, temperature sensors, pressure sensors, viscometers, and conductivity meters, may be connected to the disperser 20, tank 12, pumps 26 and 28, and lines 14, 32, 34 and 16 to monitor, control, and optimize the processes and the liquid products. Data for formulation and process development may also be gathered in this manner. Additionally, the recirculatory batch process may be controlled by a computer and/or a programmable controller. Computer controls increase repeatability in producing acceptable batches, improve operational efficiency, and aid in troubleshooting manufacturing problems.

Figure 2:
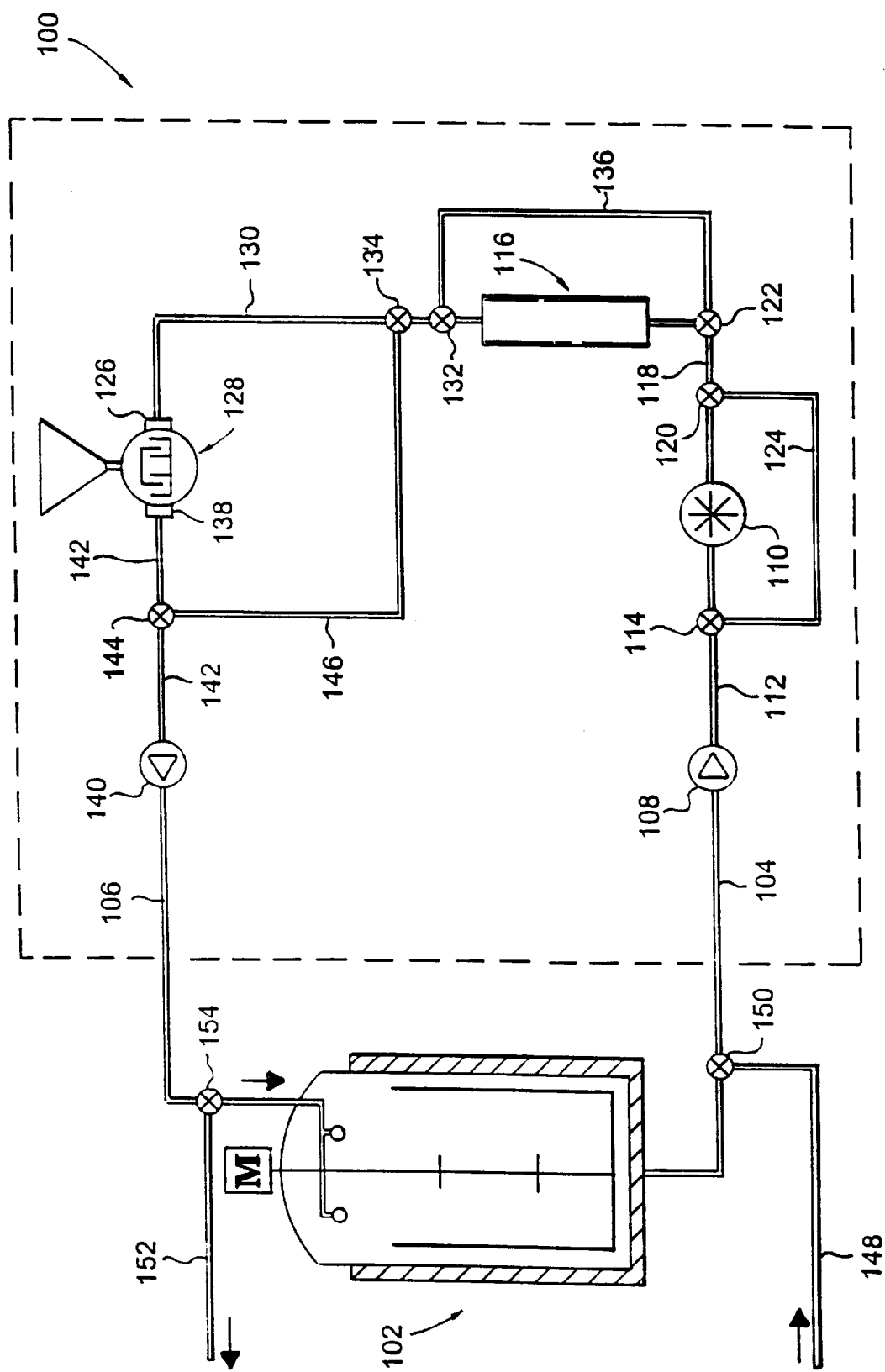
FIG. 2 is a schematic diagram of another embodiment of a recirculatory batch process system according to the present invention.

Another embodiment of the recirculatory batch processor is shown in FIG. 2. The recirculatory batch processor 100 includes a supply pump 108, a return pump 140, a homogenizer 110, a heat exchanger 116, and a solids/powder disperser 128. The recirculatory batch processor 100 is connected to a tank 102 through a supply line 104 and a return line 106. The supply line 104 is also connected to the supply pump 108. The supply pump 108 is connected to the homogenizer 110 via line 112 through valve 114. The homogenizer 110 is connected to a heat exchanger 116 via line 118 through valves 120 and 122. Valve 120 is in closer proximity to the homogenizer 110 than valve 122. A line 124 is in communication with valves 114 and 120 to permit the liquid solution to bypass the homogenizer 110.

The heat exchanger 116 is in communication with a first inlet 126 of the disperser 128 via line 130 through valves 132 and 134. Valve 132 is in closer proximity to the heat exchanger 116 than valve 134. A line 136 is in communication with valves 122 and 132 to permit the liquid solution to bypass the heat exchanger 116.

An outlet 138 of the disperser 128 is connected to the return pump 140 via line 142 through a valve 144. A line 146 is in communication with valves 134 and 144 to permit the liquid solution to bypass the disperser 128.

A valve 150 is attached to the supply line 104. Material inlet line 148 is connected to the supply line 104 through valve 150 to permit entry of liquid feeds to be mixed into the liquid drawn from the tank 102.

A valve 154 is attached to the return line 106. Line 152 is attached to valve 154 to permit removal of products from the processor 100.

Liquid is drawn from tank 102 through supply line 104 by the supply pump 108. Bypass lines 124, 136 and 146 are present to permit bypassing of the fluid stream around the homogenizer 110, heat exchanger 116, and disperser 128, respectively. Material circulating through the processing loop is returned to tank 102 by return pump 140 via return line 106.

Figure 3:
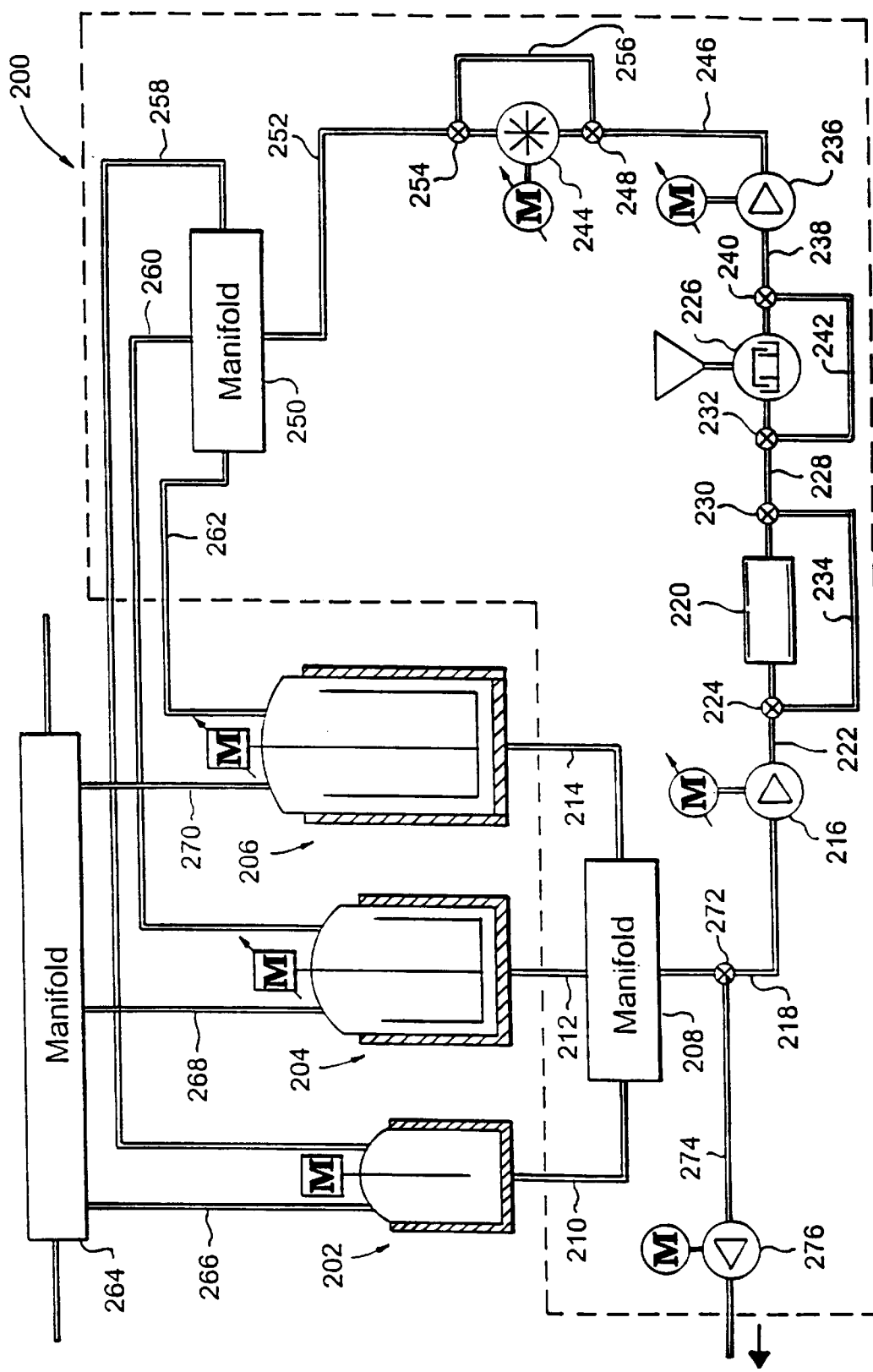
FIG. 3 is a schematic diagram of yet another embodiment of a recirculatory batch process system according to the present invention.

Another embodiment of the recirculatory batch processor is shown in FIG. 3. As shown, the recirculatory batch processor 200 is interfaced with three tanks, 202, 204 and 206. The three tanks 202, 204, and 206 are in communication with a manifold 208 via lines 210, 212, and 214, respectively. The manifold 208 is connected to a supply pump 216 through a supply line 218.

A heat exchanger 220 is in communication with the supply pump 216 via line 222 through a valve 224. The heat exchanger 220 is connected to a disperser 226 via line 228 through valves 230 and 232. Valve 230 is in closer proximity to the heat exchanger 220 than valve 232. A line 234 is in communication with valves 224 and 230 to permit the liquid solution to bypass the heat exchanger 220.

The disperser 226 is in communication with a return pump 236 via line 238 through valve 240. A line 242 is in communication with valves 232 and 240 to permit the liquid solution to bypass the disperser 226.

The return pump 236 is connected to a homogenizer 244 via line 246 through a valve 248. The homogenizer 244 is in communication with manifold 250 via line 252 through valve 254. A line 256 is in communication with valves 248 and 254 to permit the liquid solution to bypass the homogenizer 244.

The manifold 250 is in communication with the tanks 202, 204, and 206 through lines 258, 260, and 262, respectively.

A valve 272 is attached to the supply line 218. Line 274 connects valve 272 to a product pump 276. The product may be withdrawn from the system by the product pump 276.

Liquid feeds are supplied to the tanks 202, 204, and 206 through manifold 264 via lines 266, 268 and 270, respectively.

Manifold 208 permits liquid to be drawn from any one of the tanks by supply pump 216. The processor 200 contains heat exchanger 220, powder disperser 226, return pump 236 and homogenizer 244. Liquid returns to the tanks via manifold 250 which permits the liquid to be switched between return lines 258, 260, and 262 for passage to tanks 202, 204 and 206, respectively. Again, the system is valved to permit routing of flows to and around the various processing units.

The use of three tanks permits greater process flexibility in permitting the production of product batches of various sizes. Furthermore, the presence of multiple tanks permits the preparation of pre-batches in one tank which may be blended into another tank for production of a final product.

The recirculatory batch process is typically practiced with a recirculatory batch processor as follows. A liquid contained in a tank is delivered at a first rate to a recirculatory batch processor. The recirculatory batch processor comprises at least one pump selected from a supply pump and a return pump, and a disperser. The pump is in communication with the disperser. During delivery of the liquid to the recirculatory batch processor at a first rate, solids are added to the liquid via the disperser to produce a liquid containing dispersed solids. During delivery of the liquid to the recirculatory batch processor, the liquid containing dispersed solids is returned to the tank at a second rate, wherein the second rate is greater than the first rate. Circulation of the liquid between the tank and the processor may be repeated until the liquid in the tank contains a pre-selected concentration of dissolved or dispersed solids. Further intermediate processing of the liquid may occur with other units such as heaters or homogenizers contained in the circulation loop, or through additional processing in the tank. At the conclusion of processing, the product may be pumped to storage or to a product filling station for filling the product in consumer packaging.

By returning the processed liquid from the disperser at a faster rate than delivering the liquid to the disperser, a vacuum is created in the disperser. The vacuum in the disperser results in more homogenous addition of solids into the liquid.

The recirculatory batch processing method permits the dispersion of a higher concentration of solids, improved aesthetics and reduced manufacturing cycling times of the liquid than addition by continuous, in-line, or batch processing methods. Moreover, liquid products produced by the recirculatory batch process exhibit greater batch-to-batch uniformity than products produced by conventional batch processing methods.

The recirculatory batch processing method may be used to produce batches as small as 50 kg. The maximum batch size is limited only by the size of the pumps, piping, and the tank volume. Also, the recirculatory batch processing hardware used for a pilot system may be adapted for use in a full-scale production system.

The recirculatory batch process is especially useful for the addition of waxy solids that have limited solubility in aqueous media. Toiletries frequently contain ingredients containing fatty moieties, which typically contain from about 12 to about 22 carbon atoms. Examples of such ingredients containing fatty moieties include fatty acids, e.g., stearic acid; fatty alcohols, e.g., stearyl alcohol; fatty esters, e.g., cetyl palmitate; fatty alkanolamides, e.g., stearic mono or diethanolamide; and the fatty esters of glycols, polyols or alkoxylated polyols such as ethylene glycol mono or distearate, glyceryl distearate and PEG-150 distearate, i.e., the distearate ester of polyethylene glycol having an average value of 150 ethylenoxy units. The latter material is also known by the technical name polyethylene glycol 6000 distearate, available from the Stepan Chemical Company of Maywood, N.J., under the tradename PEG 6000 distearate. These waxy solids typically have melting points below 100° C. They are typically incorporated into liquid formulations by heating the formulation above the melting point of the additive to dissolve or disperse the additive into the formulation. The formulation must then be cooled prior to product packaging.

The recirculatory batch process advantageously permits the incorporation of such additives without heating or cooling, offering advantages in capital costs, energy costs and cycle time.

The recirculatory batch process may also be advantageously applied to the suspension of water-insoluble inorganic additives, such as titanium dioxide, zinc oxide, magnesium silicate, or mixtures thereof, into detergent preparations.

The recirculatory batch processing method may produce products with higher concentrations of powders or solids than conventional batch processes. For example, the commercial production of an emulsion consisting of 20% by weight titanium and zinc oxides in an oil or aqueous-oil medium would be difficult to achieve in a continuous or typical batch process. However, such an emulsion may be produced with the recirculatory batch processing method and equipment of the present invention.

Also, the recirculatory batch processing method may mix solid compounds into liquids which otherwise may require the use of heat or additional mechanical devices. For example, polyethylene glycol 6000 distearate (PEG 6000 distearate) is typically heated to melting in order to be dispersed into a liquid. By dispersing PEG 6000 distearate into a liquid solution using the recirculatory batch process method and equipment described herein, no heating or use of additional mechanical devices is necessary. This reduces processing time and cost.

Furthermore, the recirculatory batch processing system may be designed to be cleaned-in-place to enhance operating efficiency. Cleaning-in-place provides a reservoir of a cleaning agent that can circulate through the tank, recirculatory batch processor and associated piping to clean the equipment when it is changed over to make a different formulation.

Because identical process technology may be used for many liquid formulations, it is possible to standardize process development, manufacturing, and validation protocols across a product line with the recirculatory batch processing method.

DESCRIPTION OF THE PREFERRED EMBODIMENT

The following examples illustrate the present invention without limitation.

EXAMPLE 1

A detergent having the composition as shown in Table 1 is prepared using the recirculatory batch process.

TABLE 1

| Ingredient Trade Name | Component Cosmetic Toiletry Fragrance Association (CTFA) Name | Function | Source | % Active | % (w/w) | % (w/w) Active |
|---|---|---|---|---|---|---|
| Flexan 130 | Sodium polystyrene sulfonate | anti-stat, conditioner | National Starch and Chemical Co. | 30.00 | 2.00 | 0.60 |
| Chembetaine | Cocamidopropylbetaine | foam booster/ viscosity builder | Chemron | 35.00 | 7.00 | 2.45 |
| | Cocamide DEA | | | 100.00 | 5.00 | 5.00 |
| Polymer JR 125 | Polyquaternium 10 | conditioner | Amerchol | 100.00 | 0.20 | 0.20 |
| Hampene 220 | Tetrasodium EDTA | chelator | Hampshire | 100.00 | 0.20 | 0.20 |
| Citric acid | Citric acid | pH adjustment | | 100.00 | 0.20 | 0.20 |
| | Sodium laureth sulfate | cleansing | | 27.00 | 20.00 | 5.40 |
| | Ammonium lauryl sulfate | cleansing | | 30.00 | 25.00 | 7.50 |
| dl Panthenol | Panthenol | conditioner | Roche | 50.00 | 1.00 | 0.50 |
| Hydrotriticum WAA | Wheat amino acids | conditioner | Croda | 30.00 | 0.50 | 0.15 |
| Monaquat TG | Bis-hydroxyethyl dihydroxypropyl stearaminium chloride | conditioner | Mona | 50.00 | 0.70 | 0.35 |
| DC 8220 | Trimethylsily amodimethicone | conditioner | Down Corning | 100.00 | 0.25 | 0.25 |
| Witch Hazel | Witch Hazel | astringent | | | 1.50 | 0.00 |
| Glydant | DMDM Hydantoin | preservative | Lonza | | 0.30 | |
| | Water | | | | 36.15 | |

The shampoo was made in the recirculatory batch process shown in FIG. 1. 1,446 pounds of water (Item 15) were charged to tank 12, followed by 80 pounds of Flexan 130 (Item 1) and 280 pounds of Chembetaine (Item 2). The mixture was stirred at ambient temperature for about 5 minutes. Pumps 26 and 28 and disperser 20 were started and the material from the tank was circulated through the recirculatory batch processor. 8 pounds of Ucare Polymer JR 125 (Item 4) were added into the disperser. After all of the Ucare Polymer JR 125 had been incorporated into the liquid, the temperature in the tank was increased to about 65° C. and the contents of the tank were maintained at that temperature with stirring for about 30 minutes. 8 pounds of citric acid (Item 6) and 8 pounds of Hampene 220 (Item 5) were then added sequentially to the disperser. After adding the Hampene 220, heating was discontinued and 1000 pounds of ammonium lauryl sulfate (Item 8), 800 pounds of sodium laureth sulfate (Item 7) and 200 pounds of cocamide DEA (Item 3) were then added sequentially with agitation. 28 pounds of Monaquat TG (Item 11) were added, followed by 10 pounds of DC 8220 (Item 12), 40 pounds of dl panthenol (Item 9), 20 pounds of hydrotriticum WAA (Item 10), 60 pounds of witch hazel (Item 13) and 12 pounds of Glydant (Item 14). Agitation was continued until the product cooled to below about 35° C. The product was then transferred to the packaging line. The resultant shampoo was clear and has a pH of 5.95.

Attenuated total reflectance fourier transform infrared (ATR-FTIR) spectroscopy was performed on a shampoo prepared as above to measure the relative amount of organic residue left on hair swatches after application of the shampoo.

A hair swatch was prepared by binding about 1.0 gram of hair (each hair at least about 2 inches in length) with wire. The hair swatch was washed and extracted for about 3 minutes in about 100 ml of an 80:20 ethanol-water solution, at least 7 times. The 80:20 ethanol-water solution was prepared by mixing about 80 ml of ethanol with about 20 ml water.

About 0.5 ml Aquanet, a styling product, was applied to the hair of the hair swatch. The hair swatch was then blow dried. About 0.5 ml Loreal Forta VIVE shampoo was applied to the hair. Then, about 0.5 ml Pantene Pro-V conditioner was applied to the hair. The hair was blow dried again. The styling product, shampoo, and conditioner were applied uniformly on front and back of the hair using thumb and index fingers. This procedure was repeated 7 times to simulate residue build-up due to a week-long daily use of hair care products.

A methylparaben solution was prepared by diluting about 2 mg of methylparaben with about 1 ml of the 80:20 ethanol-water solution.

The methylparaben solution exhibits nearly no absorbance around 2950 $cm^{-1}$, which correspond to $CH_2$, while exhibiting absorbance around 1688 $cm^{-1}$, which corresponds to C=O. The absorbance around 1688 $cm^{-1}$ was used as a reference in the ATR-FTIR measurements.

About 100 ml of the hair (each hair 1 cm in length) was cut from the hair swatch and extracted in about 2 ml of an 80:20 ethanol-water solution for about 2 minutes.

Following the extraction, 0.9 ml of the extract was combined with 0.10 ml of the methylparaben solution. The extract was then assayed using ATR-FTIR. The ATR window was a zinc selenium window crystal embedded into a plate. The absorbance of the extract was measured at 1280 $cm^{-1}$, 1688 $cm^{-1}$, and 2950 $cm^{-1}$ which correspond to C—O, C=O, and $CH_2$, and the absorption ratios of $CH_2$ to C=O and $CH_2$ to C—O were calculated. The $CH_2$ absorbance was primarily a result of organic residues in the extract.

The hair swatch was then rinsed with tap water at about 38° C. and 40 ml/second for about 6 seconds. About 0.5 ml of the shampoo prepared above was applied to the hair swatch and lathered for about 2 minutes. The hair swatch was then rinsed for about 10 seconds. Rinsing was performed by holding the hair swatch vertically at the bound end under running water with one hand while splaying the hair with the thumb and index finger of the other hand. About 0.5 ml of the shampoo was applied again to the hair swatch and lathered for about 2 minutes. The hair swatch was rinsed again for about 10 seconds and dried using a fan for at least about 3 hours.

After the hair swatch was dried, about 100 ml of the hair (each hair 1 cm in length) was cut from the hair swatch and extracted in about 2 ml of an 80:20 ethanol-water solution for about 2 minutes.

Following the extraction, about 0.9 ml of the extract was combined with about 0.10 ml of the methylparaben solution. The extract was then assayed using ATR-FTIR. The absorbance of the extract was measured at 1280 cm$^{-1}$, 1688 cm$^{-1}$, and 2950 cm$^{-1}$ and the absorption ratios of $CH_2$ to C=0 and $CH_2$ to C—0 were calculated.

The shampoo prepared above was tested on virgin brown hair and dry damaged bleached hair made by DeMao Brothers Inc. Three test runs were performed for each type of hair. The results are shown in Table 2. Each value shown in Table 2 is the average of the three test runs.

TABLE 2

| | % Residue Removal | |
|---|---|---|
| Absorption Ratio | Virgin Brown Hair | Dry Damaged Bleached Hair |
| $CH_2$ to C=O | 77 ± 7 | 94 ± 2 |
| $CH_2$ to C—O | 76 ± 7 | 93 ± 3 |

Approximately 94% of the organic residue in the dry damaged bleached hair was removed from the hair by the shampoo.

ATR-FTIR spectroscopy was also performed to determine the rinsability of the shampoo as compared to Pantene Pro-V for Normal Hair and Pantene Pro-V Daily Clarifying. The same ATR-FTIR equipment was used as described above. The following test was performed with the shampoo prepared above, Pantene Pro-V for Normal Hair, and Pantene Pro-V Daily Clarifying.

Hair swatches were prepared by binding about 1.0 gram of dry damaged bleached hair (each hair at least about 2 inches in length) made by DeMao Brothers Inc. with wire. A hair swatch was washed and extracted for about 3 minutes in about 100 ml of an 80:20 ethanol-water solution, at least 7 times. The rinsate, i.e., the washing solution, was assayed using the ATR-FTIR spectrometer. The absorbance of the rinsate was less than 0.10 at 2950 cm$^{-1}$, which corresponds to $CH_2$.

The hair swatch was allowed to dry using a fan for at least about 3 hours. The hair swatch was then rinsed with tap water at about 38° C. and 40 ml/second for about 6 seconds. About 0.5 ml of the shampoo prepared above was applied to the hair swatch and lathered for about 2 minutes. The hair swatch was then rinsed for about 6 seconds. Rinsing was performed by holding the hair swatch vertically at the bound end under running water with one hand while splaying the hair with the thumb and index finger of the other hand. About 0.5 ml of the shampoo was applied again to the hair swatch and lathered for about 2 minutes. The hair swatch was rinsed again for about 6 seconds and the hair swatch was dried using a fan for at least about 3 hours.

After the hair swatch was dried, about 100 ml of the hair (each hair 1 cm in length) was cut from the hair swatch and extracted in about 2 ml of an 80:20 ethanol-water solution for about 2 minutes.

A methylparaben solution was prepared by diluting about 2 mg of methylparaben with about 1 ml of an 80:20 ethanol-water solution.

Following the extraction, about 0.9 ml of the extract was combined with about 0.10 ml of the methylparaben solution. The extract was then assayed using ATR-FTIR. The absorbance of the extract was measured at 1688 cm$^{-1}$ and 2950 cm$^{-1}$, which correspond to C=O and $CH_2$, respectively, and the absorption ratio of $CH_2$ to C=O was calculated.

The $CH_2$ to C=O absorption ratio as a function of concentration of organic residue in each shampoo was determined by the following procedure. Sample solutions containing 0.5 mg/ml, 0.2 mg/ml, 0.1 mg/ml, 0.05 mg/ml, and 0.01 mg/ml shampoo and 0.2 mg/ml of methylparaben diluted in 80:20 ethanol-water solution were prepared. The absorbance ratio of $CH_2$ to C=O was determined by ATR-FTIR as described above for each sample solution. Based upon the $CH_2$ to C=O absorbance ratios for each shampoo, a linear equation for each shampoo was determined relating the $CH_2$ to C=O absorption ratio to the concentration of shampoo present in the sample solution. The concentration of the shampoo represented the concentration of organic residues in the sample solution.

The amount of organic residue present in the extracts was calculated from the measured $CH_2$ to C=O absorbance ratio of the extract and the linear relationship determined for each shampoo. The results are shown in Table 3.

TABLE 3

| Shampoo | Residue Extracted From Hair (mg/ml) |
|---|---|
| Shampoo prepared above and described in Table 1 | 0.281 |
| Pantene Pro-V for Normal Hair | 0.822 |
| Pantene Pro-V Daily Clarifying | 1.99 |

The shampoo prepared above and described in Table 1 left less than 40% the amount of organic residue that Pantene Pro-V for Normal Hair left and less than 20% the amount of organic residue that Pantene Pro-V Daily Clarifying left.

EXAMPLE 2

A shampoo formulation which includes polyethylene glycol 6000 distearate having the components shown in Table 4 was prepared.

TABLE 4

| Item | Component | % by Weight Based Upon Total Weight of the Shampoo |
|---|---|---|
| 1 | Polyoxyethylene 80 Sorbitan Monolaurate | 5.500 |
| 2 | Polyethylene Glycol 6000 Distearate | 0.500 |
| 3 | Ucare Polymer JR-400 | 0.1425 |
| 4 | Purified Water, USP | 63.946 |
| 5 | Sodium Laureth-13 Carboxylate | 0.475 |
| 6 | Cocamidopropyl Betaine | 13.300 |
| 7 | Lauric Myristic Imidazoline (30%) | 2.850 |
| 8 | Sodium Tridecyl 3 Sulfate (30%) | 9.500 |
| 9 | Glycerin 917, USP | 1.900 |
| 10 | Polyoxyethylene 80 Sorbitan Monolaurate | 1.000 |
| 11 | Fragrance | 0.275 |
| 12 | Purified Water, USP | 0.100 |
| 13 | Quaternium 15 | 0.05 |
| 14 | Purified Water, USP | 0.100 |
| 15 | Color | 0.000242 |
| 16 | Color | 0.000226 |
| 17 | Tetrasodium EDTA Solution | 0.137 |
| 18 | Purified Water, USP | 0.112 |
| 19 | Citric Acid Anhydrous | 0.112 |

The shampoo was made according to the following procedure using the apparatus of FIG. 2.

Sodium Laureth-13 Carboxylate (Item 5) was pre-melted.

Citric Acid solution was prepared by measuring water (Item 18) in a stainless steel pot. Citric Acid (Item 19) was added and Items 18 and 19 were mixed until dissolved.

Dowicil solution was prepared by measuring water (Item 12) in a stainless steel pot. Quaternium 15 (Item 13) was added, and Items 12 and 13 were mixed until dissolved.

Fragrance premix was prepared by charging polyoxyethylene 80 sorbitan monolaurate (Item 10) to an appropriately sized kettle or drum. Fragrance (Item 11) was added, and the resultant mixture was mixed for at least 15 minutes or until the mixture was clear.

Polyoxyethylene 80 sorbitan monolaurate (Item 1) was charged to the compounding tank. Recirculation of the batch through the processor was begun by turning on the supply and return pumps and the powder disperser. Polyethylene glycol 6000 distearate (Item 2) and Ucare Polymer JR-400 (Item 3) were then added sequentially through the disperser funnel. The batch was recirculated through the disperser until the solids were dissolved after which the pumps and disperser were shut down. Water (item 4) is then added to tank, and the mixer was started. Mixing was continued for about 10 minutes. The recirculation pumps were restarted, and the premelted Sodium Laureth-13 Carboxylate (Item 5) was added. After the premelted Sodium Laureth-13 Carboxylate was added, recirculation was continued for about an additional two minutes after which recirculation was stopped. Cocoamidopropyl Betaine (item 6) was added to the tank. The tank contents were then mixed for about 10 minutes with the tank agitator. After the addition of the Cocoamidopropyl Betaine, the following ingredients were added in order:

Lauric Myristic Imidazoline (30%) (Item 7)
Sodium Tridecyl 3 Sulfate (30%) (Item 8)
Glycerin 917, USP (Item 9)

The recirculation pumps were once again turned on and the following ingredients were added:

Fragrance Premix
Dowicil Solution
Colors (Items 15 and 16)
Versene 100XL
Citric Acid Solution After the addition of the above ingredients, recirculation was continued for about 3 minutes and then the recirculation pumps were turned off. The batch was mixed for at least about 10 minutes until the batch was homogeneous. Citric acid solution was added to adjust the pH of the batch to a value of about 6.0 to about 6.4. A clear shampoo was obtained. The process of the invention permits the preparation of the batch without heating and cooling, permitting a reduction in cycle time.

EXAMPLE 3

A sunscreen product that is an oil-in-water emulsion containing suspended inorganic sunscreen particles was made in the equipment shown in FIG. 3 using only one of the tanks. All parts of the formulation are given in parts by weight to make 100 parts of the overall formulation. 68.05 parts of water were charged to the tank. The supply and return pumps and powder disperser were activated, and the ingredients in Table 5 were charged sequentially to the powder disperser.

TABLE 5

| Parts | Tradename | CTFA Name |
|---|---|---|
| 0.05 | | disodium EDTA |
| 0.1 | Carbopol 940 | Carbomer 940 |
| 0.25 | Pemulen TR-1 | Acrylate/C10-30 Alkyl Acrylates crosspolymer |

The powder disperser was deactivated after the powders in Table 5 were added. 3.0 parts propyleneglycol were added to the tank and heating of the tank contents was commenced. When the temperature of the tank contents reaches about 75° C., the ingredients in Table 6 were charged to the top of the tank with agitation.

TABLE 6

| Parts | Tradename | CTFA Name |
|---|---|---|
| 1.0 | Neo Heliopan | OS octyl salicylate |
| 6.5 | Neo Heliopan AV | octyl methoxycinnamate |
| 0.5 | Fluid 200/50 CS | dimethicone |
| 5.0 | Finsolv TN | C12-C15 alkylbenzoate |
| 4.0 | Wickenol 131 | isopropyl isostearate |
| 0.1 | Vitamin E Acetate | tocopheryl acetate |
| 2.75 | | benzophenone-3 |
| 0.5 | Synchrowax HR-C | tribehenin |
| 0.5 | | cetyl palmitate |
| 0.5 | | stearyl alcohol |
| 1.5 | Antaron WP660 | tricontanyl PVP |

Heating was continued. When the batch reaches a temperature of about 80° C., the powder disperser was activated, and 1.0 part titanium dioxide was added through the disperser. Following the addition of the titanium dioxide, the disperser was deactivated. 0.3 part Tween 60 polysorbate 60 and 1.5 parts Amphisol DEA-cetylphosphate were added through the top of the tank. The homogenizer was activated, and fluid from the tank was circulated through the processor until one tank volume had circulated through the homogenizer. A solution of 1.0 part water and 0.5 part triethanolameine was added, and the batch was agitated at high speed for about 10 minutes. Heating of the batch was discontinued, and material from the tank was circulated through the heat exchanger on the processor until the batch reached a temperature of about 35° C. A solution of 0.1 part Dowicil 200 quaternium 15 in 1.0 part water was added to the batch along with 0.3 part fragrance. Stirring was continued until the batch was homogeneous and the product was then piped to product storage.

All patents, publications, applications, and test methods mentioned above are hereby incorporated by reference.

Many variations of the present matter will suggest themselves to those skilled in the art in light of the above detailed description. All such obvious variations are within the patented scope of the appended claims.

What is claimed is:

1. A single phase detergent composition comprising:
   (a) a first anionic surfactant;
   (b) the anionic polymer sodium polystyrene sulfonate;
   (c) a mono cationic conditioning agent selected from the group consisting of bishydroxyethyldihydroxypropyl stearaminium chloride and cetrimonium chloride; and
   (d) a cationic polymer selected from the group consisting of polyquaternium 10 and polyquaternium 11 such that said cationic polymer does not produce an insoluble precipitate with said anionic polymer in said composition,
   whereby said composition is clear in the absence of a coloring agent or tinting agent.

2. A detergent composition as defined in claim 1, further comprising (e) a second anionic surfactant.

3. A detergent composition as defined in claim 1, wherein said detergent composition is a shampoo.

4. A detergent composition as defined in claim 2, wherein said first anionic surfactant comprises ammonium lauryl sulfate and said second anionic surfactant comprises sodium laureth sulfate.

5. A detergent composition as defined in claim 1, wherein said mono cationic conditioning agent comprises bishydroxyethyldihydroxypropyl stearaminium chloride.

6. A detergent composition as defined in claim 1, wherein said cationic polymer is a substituted cationic polymer having a substitute range from about 0.3 to about 0.6.

7. A detergent composition as defined in claim 1, wherein said cationic polymer has a molecular weight of about 300,000.

8. A detergent composition as defined in claim 1, wherein said cationic polymer comprises polyquaternium 10 having a cationic substitution ranging from about 0.3 to about 0.6.

9. A detergent composition as defined in claim 1, wherein the weight ratio of said anionic polymer to said cationic polymer ranges from about 5:1 to about 1:1.

10. A detergent composition as defined in claim 1, having a pH ranging from about 5.5 to about 6.5.

11. A detergent composition as defined in claim 2, further comprising:
    (f) an anti-oxidant;
    (g) a humectant;
    (h) a foam stabilizer;
    (i) a metal chelator;
    (j) water;
    (k) an anti-microbial;
    (l) a UV-absorbent;
    (m) a cationic silicone;
    (n) a preservative;
    (o) a fragrance;
    (p) a colorant;
    (q) an amphoteric surfactant; or
    (r) any combination of any of the foregoing.

12. A single phase detergent composition comprising:
    (a) a surfactant and styling residue removing effective amount of a combination (i) ammonium lauryl sulfate and (ii) sodium laureth sulfate;
    (b) a cationic build-up removing effective amount of sodium polystyrene sulfonate;
    (c) a dry-hair conditioning effective amount of bishydroxyethyldihydroxypropyl stearaminium chloride; and
    (d) a hair conditioning effective amount of polyquaternium 10, whereby said composition is clear in the absence of a coloring agent or tinting agent.

13. A method for cleaning hair, said method comprising applying to hair in need of cleaning, a hair cleaning effective amount of a shampoo as defined in claim 1.

14. A method for reducing residue in hair, said method comprising applying to hair in need of reducing residue, a hair residue reducing effective amount of a detergent composition as defined in claim 3.

15. A single phase detergent composition prepared by the process comprising:
    (a) diluting the anionic polymer sodium polystyrene sulfonate in water and betaine, wherein the weight ratio of anionic polymer to water ranges from about 1:50 to about 1:70, and the weight ratio of anionic polymer to betaine range from about 1:10 to about 1:15 to yield a first mixture;
    (b) stirring said diluted anionic polymer;
    (c) adding a cationic polymer selected from the group consisting of polyquaternium 10 and polyquaternium 11 such that said cationic polymer does not produce an insoluble precipitate with said anionic polymer in said composition to said stirred, diluted anionic polymer at ambient temperature and pressure to yield a second mixture;
    (d) heating said second mixture to a temperature ranging from about 60° C. to about 70° C.;
    (e) adding a chelator and a pH buffer to said heated second mixture while maintaining heating at a temperature ranging from about 60° C. to about 70° C.;
    (f) discontinuing heating said second mixture;
    (g) adding an anionic surfactant and a thickener to said second mixture while stirring to yield a third mixture; and
    (h) adding a mono cationic conditioning agent selected from the group consisting of bishydroxyethyldihydroxypropyl stearaminium chloride and cetrimonium chloride, whereby said composition is clear in the absence of a coloring agent or tinting agent.

* * * * *